US00PP17855P2

(12) United States Plant Patent
Hoek

(10) Patent No.: US PP17,855 P2
(45) Date of Patent: Jul. 10, 2007

(54) ***CHRYSANTHEMUM* PLANT NAMED 'NOA'**

(50) Latin Name: *Chrysanthemum×morifolium*
Varietal Denomination: Noa

(75) Inventor: Jan Hoek, 's-Gravenzande (NL)

(73) Assignee: Deliflor Chrysanten B.V., Maasdijk (NL)

( * ) Notice: Subject to any disclaimer, the term of this patent is extended or adjusted under 35 U.S.C. 154(b) by 93 days.

(21) Appl. No.: 11/178,270

(22) Filed: Jul. 8, 2005

(51) Int. Cl.
*A01H 5/00* (2006.01)

(52) U.S. Cl. ..... Plt./294

(58) Field of Classification Search ..... Plt./294
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Chrysanthemum* plant named 'Noa', characterized by its daisy-type inflorescences with white-colored elongated oblong ray florets and bright green-colored disc florets; dark green-colored foliage; strong and upright flowering stems; early, uniform and freely flowering habit; and good postproduction longevity.

2 Drawing Sheets

Botanical designation: *Chrysanthemum×morifolium.*
Cultivar denomination: 'Noa'.

BACKGROUND OF THE INVENTION

The present invention relates to a new and distinct cultivar of *Chrysanthemum* plant, botanically known as *Chrysanthemum×morifolium* and referred to by the name 'Noa'.

The new *Chrysanthemum* is the product of a planned breeding program conducted by the Inventor in 's-Gravenzande, The Netherlands. The objective of the breeding program is to create new cut *Chrysanthemum* cultivars with interesting inflorescence forms and attractive floret coloration.

The new *Chrysanthemum* originated from a cross-pollination made by the Inventor in 2002 in 's-Gravenzande, The Netherlands, of an unnamed proprietary *Chrysanthemum* selection, not patented, as the female, or seed, parent with an unnamed proprietary *Chrysanthemum* selection, not patented, as the male, or pollen, parent. The new *Chrysanthemum* was discovered and selected by the Inventor as a single plant within the progeny of the stated cross-pollination in a controlled environment in 's-Gravenzande, The Netherlands.

Asexual reproduction of the new *Chrysanthemum* by terminal cuttings in 's-Gravenzande, The Netherlands since 2002, has shown that the unique features of this new *Chrysanthemum* are stable and reproduced true to type in successive generations.

BRIEF SUMMARY OF THE INVENTION

The cultivar Noa has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Noa'.

These characteristics in combination distinguish 'Noa' as a new and distinct cultivar:

1. Daisy-type inflorescences with white-colored elongated oblong ray florets and bright green-colored disc florets.
2. Dark green-colored foliage.
3. Strong and upright flowering stems.
4. Early, uniform and freely flowering habit.
5. Good postproduction longevity.

Plants of the new *Chrysanthemum* differ primarily from plants of the parent selections in inflorescence form and floret color.

Plants of the new *Chrysanthemum* can be compared to plants of the *Chrysanthemum* cultivar White Reagan, disclosed in U.S. Plant Pat. No. 8,784. In side-by-side comparisons conducted in Hensbroek, The Netherlands, plants of the new *Chrysanthemum* differed primarily from plants of the cultivar White Reagan in the following characteristics:

1. Flowering stems of plants of the new *Chrysanthemum* were cylindrical than flowering stems of plants of the cultivar White Reagan.
2. Plants of the new *Chrysanthemum* flowered earlier than plants of the cultivar White Reagan.
3. Plants of the new *Chrysanthemum* had more inflorescences per flowering stem than plants of the cultivar White Reagan.
4. Plants of the new *Chrysanthemum* had fewer ray florets per inflorescence than plants of the cultivar White Reagan.
5. Disc florets of plants of the new *Chrysanthemum* retained green coloration longer than disc florets of plants of the cultivar White Reagan.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Chrysanthemum.*

The photograph on the first sheet comprises a side perspective view of a typical flowering stem of 'Noa'.

The photograph at the top of the second sheet is a close-up view of typical inflorescences of 'Noa'.

The photograph at the bottom of the second sheet comprises a close-up view of the upper and lower surfaces of typical inflorescences and leaves of 'Noa'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in 's-Gravenzande, The Netherlands, under commercial practice in a glass-covered greenhouse. Plants were initially given long day/short night treatments followed by short day/long night treatments to induce flower initiation and development. Average day and night temperatures were 18 and 19° C., respectively. Plants were not pinched and were grown as single stem spray-types.

Botanical classification: *Chrysanthemum×morifolium* cultivar Noa.

Commercial classification: Daisy-type *Chrysanthemum* typically grown as a spray-type cut flower.

Parentage:

*Female or seed parent.*—Unnamed proprietary selection of *Chrysanthemum×morifolium,* not patented.

*Male or pollen parent.*—Unnamed proprietary selection of *Chrysanthemum×morifolium,* not patented.

Propagation:

*Type.*—Terminal tip cuttings.

*Time to initiate roots, summer.*—About 10 days at 20° C.

*Time to initiate roots, winter.*—About 14 days at 20° C.

*Root description.*—Fine, fibrous; white in color.

*Rooting habit.*—Freely branching.

Plant description:

*Appearance.*—Herbaceous daisy-type cut *Chrysanthemum;* typically grown as a single stem spray-type. Upright and strong flowering stems.

*Growth rate.*—Rapid; vigorous.

*Crop time.*—For cut flowers, about 78 and 124 days are required to produce flowering stems during the summer and winter, respectively.

*Flowering stem description.*—Length: About 90 cm. Diameter, at apex: About 6.5 mm. Strength: Strong. Aspect: Upright. Color: 146B.

*Foliage description.*—Arrangement: Alternate; simple. Quantity of leaves per main stem: About 26 to 32. Length: About 8.5 to 12 cm. Width: About 6.5 to 10 cm. Apex: Mucronate. Base: Attenuate to rounded. Margin: Palmately lobed. Texture, upper and lower surfaces: Rough; pubescent. Petiole length: About 2.5 to 4 cm. Color: Developing foliage, upper surface: 147A. Developing foliage, lower surface: Close to 147B. Fully expanded, upper surface: Between 137A and 147A. Fully expanded, lower surface: Close to 147B. Venation, upper surface: 146A. Venation, lower surface: 146B. Petiole, upper and lower surfaces: 146B.

Inflorescence description:

*Appearance.*—Daisy-type inflorescence form. Inflorescences borne on terminals, arising from leaf axils. Ray and disc florets develop acropetally on the receptacle.

*Flowering response.*—Under natural conditions, plant typically flower in November in the Northern Hemisphere. At other times of the year, inflorescence initiation and development can be induced under short day/long night conditions (at least 13 hours of darkness). Plants exposed to long day/short night conditions after planting followed by photoinductive short day/long night conditions flower about eight weeks later.

*Postproduction longevity.*—Inflorescences will maintain good substance and form for about 3.5 weeks after harvesting.

*Quantity of inflorescences per flowering stem.*—About 20 inflorescences per flowering stem.

*Inflorescence size.*—Diameter: About 6.5 cm. Depth (height): About 2 cm. Diameter of disc: About 1.6 cm.

*Inflorescence buds.*—Length: About 1 cm. Diameter: About 1.3 cm. Shape: Oblate. Color: Close to 145D.

*Ray florets.*—Length, fully developed: About 2.8 to 3.2 cm. Width, fully developed: About 1.1 to 1.5 cm. Shape: Elongated oblong. Apex: Rounded. Base: Attenuate; fused. Texture, inner and outer surfaces: Smooth, glabrous. Number of ray florets per inflorescence: About 20 to 24 in one to two whorls. Color: When opening, upper and lower surfaces: 4D. Fully opened, upper and lower surfaces: Brighter and whiter than 155C.

*Disc florets.*—Shape: Tubular; elongated. Length: About 5 mm. Width: About 1 mm. Number of disc florets per inflorescence: About 230. Color: Immature: 144A. Mature: N144C.

*Peduncles.*—Length, terminal peduncle: About 1.7 cm. Length, fourth peduncle: About 4.2 cm. Diameter: About 3 mm. Texture: Pubescent. Aspect: About 30° from vertical. Color: 146A.

*Reproductive organs.*—Androecium: Present on disc florets only. Anther color: 15B. Amount of pollen: None observed. Gynoecium: Present on both ray and disc florets. Stigma length: About 5 mm. Stigma width: About 0.5 mm. Stigma color: Towards the apex, 9C; towards the base, close to 155C.

*Seed/fruit.*—Seed and fruit production has not been observed.

Disease/pest resistance: Resistance to known *Chrysanthemum* pathogens and pests has not been observed on plants of the new *Chrysanthemum.*

It is claimed:

1. A new and distinct cultivar of *Chrysanthemum* plant named 'Noa', as illustrated and described.

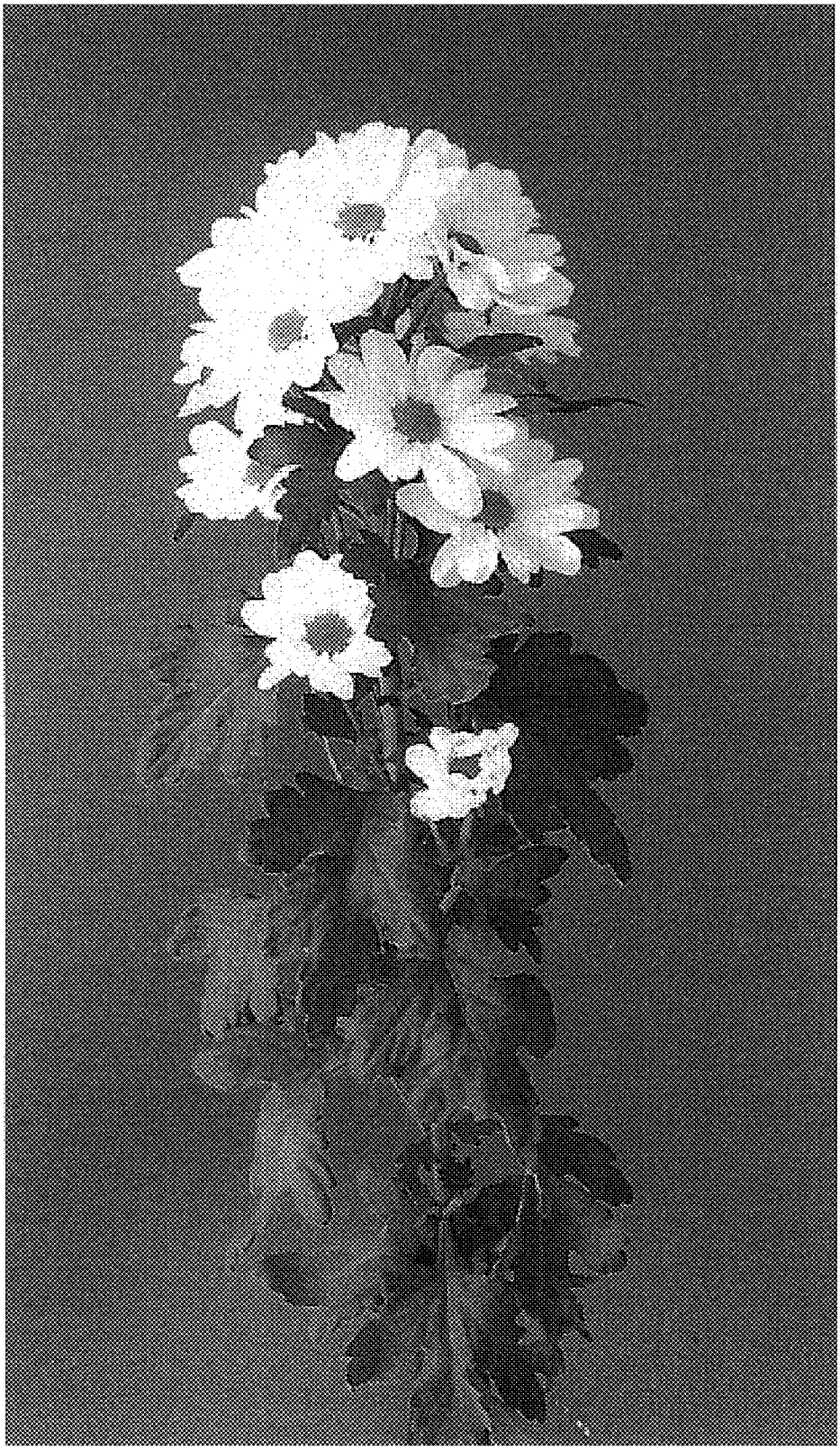

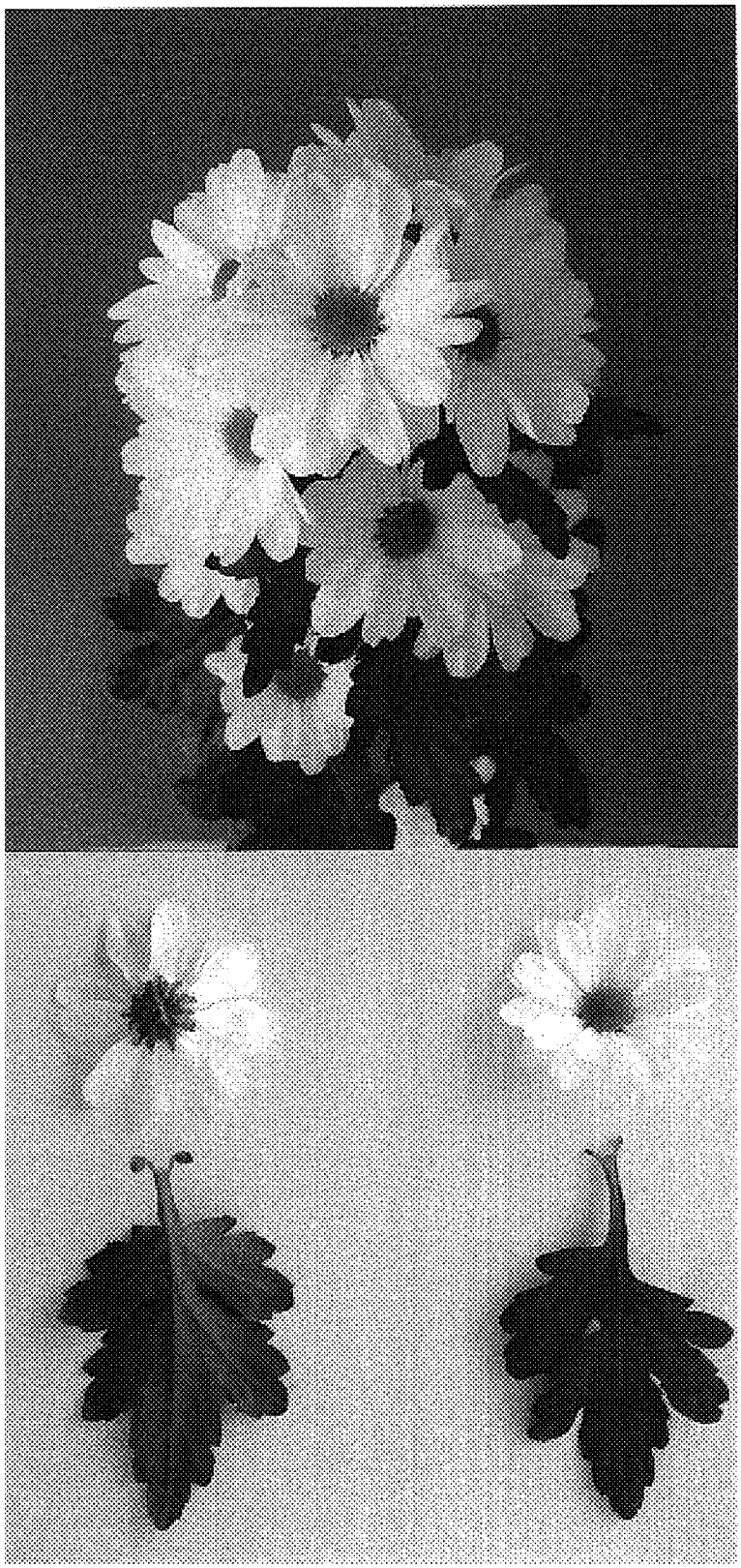

* * * * *